(12) United States Patent
Souma

(10) Patent No.: US 8,740,804 B2
(45) Date of Patent: Jun. 3, 2014

(54) BLOOD PRESSURE MEASURING CUFF, BLOOD PRESSURE MEASURING APPARATUS, BLOOD PRESSURE MEASURING METHOD, CUFF, AND CUFF MANUFACTURING METHOD

(75) Inventor: Takahiro Souma, Ashigarakami-gun (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 448 days.

(21) Appl. No.: 12/524,117

(22) PCT Filed: Jan. 18, 2008

(86) PCT No.: PCT/JP2008/050581
§ 371 (c)(1),
(2), (4) Date: Jul. 22, 2009

(87) PCT Pub. No.: WO2008/090811
PCT Pub. Date: Jul. 31, 2008

(65) Prior Publication Data
US 2010/0106031 A1     Apr. 29, 2010

(30) Foreign Application Priority Data
Jan. 24, 2007 (JP) ................................. 2007-014092

(51) Int. Cl.
*A61B 5/02* (2006.01)
(52) U.S. Cl.
USPC ........... 600/494; 600/492; 600/493; 600/485; 600/499
(58) Field of Classification Search
USPC .................. 600/490, 492, 494, 499, 485, 493
See application file for complete search history.

(56) References Cited

U.S. PATENT DOCUMENTS 2,640,502 A * 6/1953 Powers .......................... 285/114
4,210,154 A    7/1980 Klein
(Continued)

FOREIGN PATENT DOCUMENTS

| EP | 337162 A1 * | 10/1989 | ............... A61B 5/02 |
| JP | 51-118686 B | 10/1976 | |

(Continued)

OTHER PUBLICATIONS

English language translation of International Preliminary Report on Patentability issued Aug. 6, 2009 in corresponding International Patent Application No. PCT/JP2008/050581.
(Continued)

*Primary Examiner* — Michael Kahelin
*Assistant Examiner* — Tho Tran
(74) *Attorney, Agent, or Firm* — Buchanan Ingersoll & Rooney PC

(57) ABSTRACT

Provided are a blood pressure measuring apparatus capable of effectively eliminating the influence which the volume change in an upstream portion of an occluding cuff has on a pulse wave detection cuff in an oscillometric double-cuff system, increasing the S/N ratio of systolic blood pressure detection, and accurately measuring the blood pressure with an inexpensive arrangement, a cuff, and a blood pressure measuring method. The apparatus includes a first pipe (106) connected to an occluding air bag (108) and sub air bag (109). The first pipe is connected to the sub air bag, and the sub air bag is connected to the occluding air bag via an entirely foldable rod shape member (111) capable of maintaining a hollow portion. The sub air bag is laid over the occluding air bag by folding a middle pipe.

2 Claims, 8 Drawing Sheets

(56) References Cited

U.S. PATENT DOCUMENTS

| | | | | |
|---|---|---|---|---|
| 4,327,775 A | * | 5/1982 | Tally | 138/103 |
| 5,095,912 A | * | 3/1992 | Tomita | 600/485 |
| 5,306,269 A | * | 4/1994 | Lewis et al. | 604/403 |
| 2004/0024325 A1 | * | 2/2004 | Nishibayashi et al. | 600/492 |
| 2005/0035217 A1 | * | 2/2005 | Wilhite et al. | 239/398 |

FOREIGN PATENT DOCUMENTS

| | | | |
|---|---|---|---|
| JP | 53-38184 U | | 4/1978 |
| JP | 53-76586 A | | 7/1978 |
| JP | A 53-038184 | | 7/1978 |
| JP | 2-305547 A | | 12/1990 |
| JP | 2000-51162 A | | 2/2000 |
| JP | 2004-195056 A | | 7/2004 |
| JP | 2007-125247 A | | 5/2007 |
| JP | 2007125247 | * 5/2007 | A61B 5/022 |

OTHER PUBLICATIONS

International Search Report (PCT/ISA/210) for PCT/JP2008/050581 completed Jan. 29, 2008.

Written Opinion (PCT/ISA/237) for PCT/JP2008/050581 completed Jan. 29, 2008.

Japanese Office Action dated Dec. 2, 2011, issued in corresponding Japanese Patent Application No. 2007-014092. (2 pages).

* cited by examiner

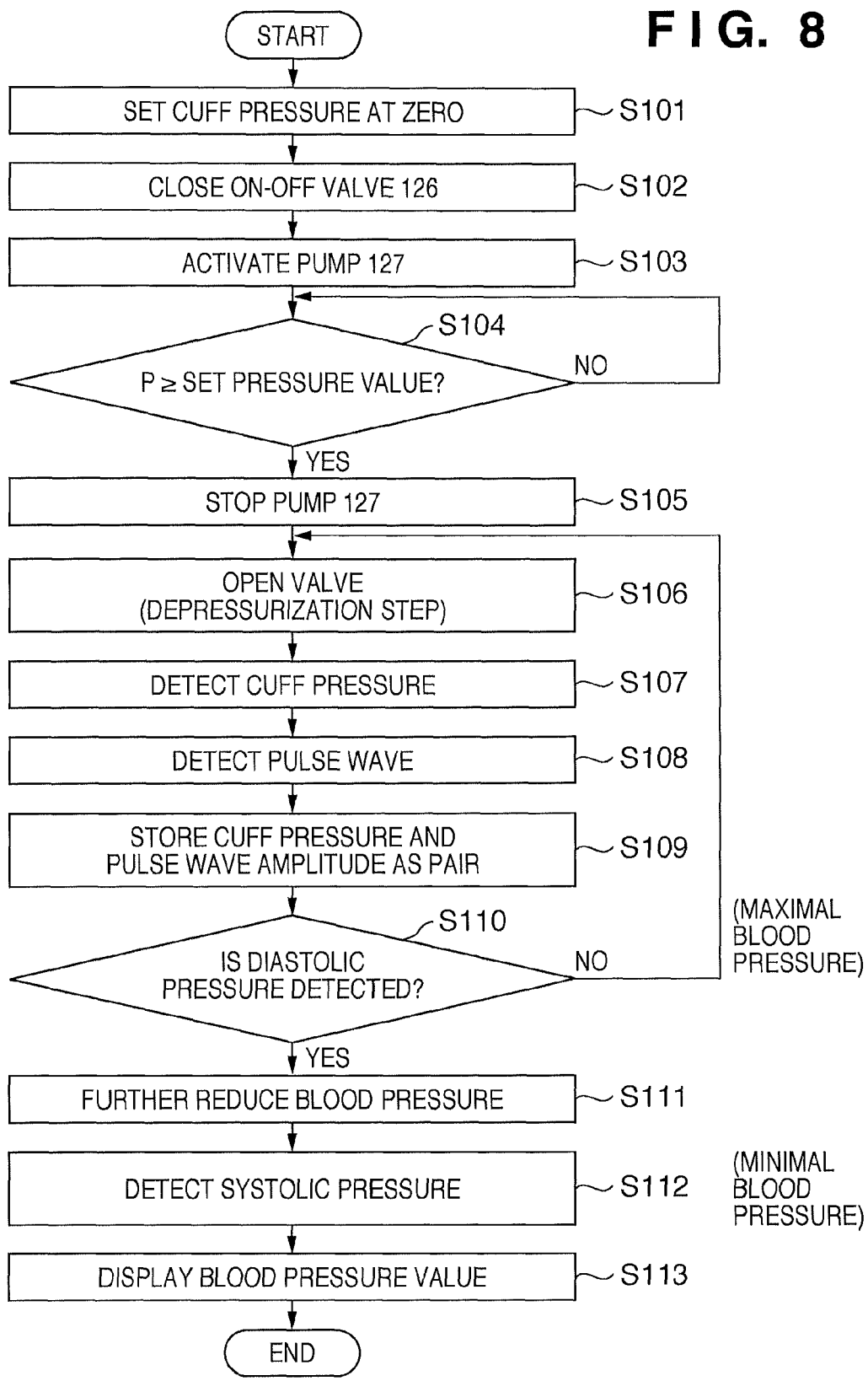

BLOOD PRESSURE MEASURING CUFF, BLOOD PRESSURE MEASURING APPARATUS, BLOOD PRESSURE MEASURING METHOD, CUFF, AND CUFF MANUFACTURING METHOD

TECHNICAL FIELD

The present invention relates to a blood pressure measuring cuff and blood pressure measuring apparatus and, more particularly, to a blood pressure measuring cuff for performing noninvasive blood pressure measurement by using the oscillometric method using an occluding cuff and a blood pressure measuring apparatus using the cuff. The present invention also relates to a blood pressure measuring apparatus, cuff, and cuff manufacturing method and, more particularly, to a technique of measuring the blood pressure by the oscillometric method by using an occluding cuff.

BACKGROUND ART

A conventional oscillometric sphygmomanometer detects the oscillation of the cuff pressure based on the volume change of the artery positioned below an occluding cuff while gradually raising the pressure of the occluding cuff to a pressure higher than the systolic blood pressure or decreasing the pressure of the occluding cuff from a pressure higher than the systolic blood pressure, and determines the systolic and diastolic blood pressure by the amplitude change of the oscillation.

The blood pressure measuring method using an occluding cuff as described above obtains the systolic blood pressure by detecting a phenomenon in which the blood flow in the artery stops flowing blood when the pressure of the occluding cuff is raised to be higher than the systolic blood pressure as a maximal pressure in the artery, and starts flowing blood when the pressure of the occluding cuff is lowered.

A presently widely used Korotkoff method (auscultatory method) obtains a systolic blood pressure value (maximal blood pressure value) by stopping the blood flow once by making the pressure of an occluding cuff higher than the systolic blood pressure, gradually decreasing the pressure of the occluding cuff, and detecting, on the downstream side of the occluding cuff, Korotkoff sounds generated at the timing at which the blood starts flowing again.

The above-mentioned oscillometric method is a method of detecting the phenomenon in which the blood starts flowing again as the pressure oscillation of an occluding cuff based on the volume change of the artery below the occluding cuff. When compared to the Korotkoff method, therefore, the oscillometric method has the advantage that the manufacturing cost can be cutting because (a stethoscope including) a sensor for sensing Korotkoff sounds is unnecessary.

The auscultatory method has the drawback that noise (scratch noise and vibrations of cuff cloth and cuff tubes) generated during blood pressure measurement is readily detected by mistake because the frequency component of the above-mentioned noise is close to that of Korotkoff sounds. On the contrary, the frequency component of the pressure oscillation is lower than that of above-mentioned noise when measurement is performed by the oscillometric method. Also, this frequency component largely differs from the noise frequency generated during blood pressure measurement, so the oscillometric method is not influenced by the noise. In addition, the oscillometric method can perform measurement even when a cuff is attached to a position deviated from the artery as a portion to be measured. Accordingly, the oscillometric method is mainly used for an automatic sphygmomanometer.

When measuring the systolic blood pressure, however, the oscillometric method has a problem caused by the blood vessel compressing characteristic of a Riva-Rocci cuff used as an occluding cuff. That is, a compressing force reflecting the cuff pressure faithfully can be obtained in a middle portion in the widthwise direction of the Riva-Rocci cuff, but a compressing force reflecting the cuff pressure faithfully can not be obtained in a portion deviated from the middle portion. The compressing force gradually reduces from the middle portion toward the end portions of the cuff and becomes zero in the end portions.

By the characteristic described above, when the cuff pressure of the occluding cuff is close to and slightly higher than the systolic blood pressure at the timing immediately before the measurement of the systolic blood pressure, the blood flow is stopped in the middle portion of the cuff. Consequently, in synchronism with the heart beat, the blood flows from the upstream portion of the occluding cuff to its middle portion and returns. By this phenomenon, a pulse wave is already detected before the generation of a pulse wave used to detect a phenomenon, as a detection target of the systolic blood pressure, in which the blood starts flowing again toward the downstream side (forearm side) of the cuff.

Also, when the cuff pressure of the occluding cuff becomes lower than the systolic blood pressure and the blood starts flowing again, this blood flow causes a volume (of artery) change downstream of the middle portion under the occluding cuff. Since the pressure of the occluding cuff is slightly lower than the arterial pressure when this volume change occurs, the blood vessel closes immediately after it has opened for a very short time. In this state, the volume change on the downstream side (part from center to downstream edge) of the occluding cuff is much smaller than that on the upstream side (part from center to upstream edge).

A pulse wave detected by the oscillometric method is based on a volume change obtained when the volume changes on the upstream and downstream sides of the occluding cuff described above are superposed. This makes it very difficult to selectively detect only the change based on the restart of the blood flow by the pulse wave especially when the blood flow amount is small. The foregoing is the cause of making the S/N ratio of systolic blood pressure measurement of the oscillometric method lower than that of the Korotkoff method.

When the cuff pressure is further lowered from the systolic blood pressure, a time during which the arterial pressure is higher than the cuff pressure gradually prolongs within one heart beat period. Since this increases the volume change on the downstream side of the cuff, the amplitude of the pulse wave gradually increases. Furthermore, although it depends on the degree of congestion of blood on the downstream side, when the internal pressure of the blood vessel in a peripheral portion of the artery from the cuff becomes higher than the cuff pressure, a reflection pressure phenomenon occurs from the periphery. This reflection abruptly increases the pulse wave.

When the cuff pressure further decreases, the time during which the internal pressure of the blood vessel in the peripheral portion from the cuff is higher than the internal pressure of the cuff prolongs. In addition, immediately before the time during which the blood vessel closes within one oscillation period disappears, the blood vessels in the upstream and downstream portions of the cuff simultaneously fully open to maximize the amplitude of the pulse wave.

In the systolic blood pressure measurement by the oscillometric method, the volume (of artery) change under the cuff at the timing of the systolic blood pressure measurement is mainly the change on the upstream side of the cuff central portion, which is equivalent to about 50% of the overall blood vessel volume under the cuff. Therefore, the timing at which the pulse wave amplitude is about 50% of a maximal pulse wave amplitude produced when almost the entire blood vessel below the cuff repeats full open and full closure is used as the systolic blood pressure.

Unfortunately, this ratio is influenced by that unbalance of the volumes in the upstream and downstream portions which is caused by the way the cuff is wrapped and contributes to the formation of the pulse wave under the cuff, a compliance difference produced by the strength with which the cuff is wrapped, the magnitude of the rise in internal pressure of the blood vessel in a peripheral portion, and the change rate. Also, the rise in internal pressure of the blood vessel in a peripheral portion is influenced by the degree of congestion of blood resulting from a short repetitive time of blood pressure measurement, but mainly influenced by the blood pressure value, the degree of peripheral circulation, and the peripheral blood vessel compliance, as differences between individual living bodies.

To solve the above problems, a triple-cuff method has been proposed as a technique in which a sub air bag is formed between an occluding air bag and measurement portion and on the upstream side (a side close to the heart when a cuff is attached to a limb) of the occluding bag, the difference between the measurement portion compressing forces of a middle portion and upstream end portion in the thrust direction of the occluding air bag (upstream end portion compressing force<middle portion compressing force) is decreased, and the entrance of a pulse wave on the upstream side is decreased when the pressure of the occluding air bag is slightly higher than the systolic blood pressure, thereby decreasing the influence of the pulse wave on the upstream side.

Patent Reference 1

Patent reference 1: Japanese Patent Laid-Open No 2004-195056

DISCLOSURE OF INVENTION

Problems that the Invention is to Solve

Accordingly, the present invention has been made in consideration of the above situation, and has as its object to increase the S/N ratio for detecting the systolic blood pressure by more effectively eliminating the influence of the volume change in an upstream portion of an occluding cuff with respect to a pulse wave detection cuff when using the oscillometric method. It is another object of the present invention to provide a blood pressure measuring apparatus which can be inexpensively obtained by forming a rod shape. member to be inserted in a communicating portion between a sub air bag and occluding air bag in an oscillometric double-cuff sphygmomanometer, and can accurately measure the blood pressure. The present invention also provides a cuff and a method of manufacturing the same.

Means of Solving the Problems

To solve the above problems, according to the present invention, there is provided a blood pressure measuring apparatus comprising a cuff main body including a cuff member configured to be attached to and detached from a blood pressure measurement portion, an occluding air bag which is laid on a side of the cuff member which is in contact with the blood pressure measurement portion and compresses the whole blood pressure measurement portion, a sub air bag which is laid on a side of the occluding air bag which is in contact with the blood pressure measurement portion and compresses a side of the blood pressure measurement portion which is close to a heart, and a pulse wave detection air bag which is laid on the side of the occluding air bag which is in contact with the blood pressure measurement portion, compresses a downstream side of a blood vessel in the blood pressure measurement portion, and detects a pulse wave on the downstream side, and pressurizing/depressurizing unit that is connected to the cuff main body via a pipe and pressurizes and depressurizes the cuff main body, the pipe including a first pipe connected to the occluding air bag and the sub air bag, a second pipe connected between the pulse wave detection air bag and cuff pressure detecting unit that obtains a cuff pressure signal from a pressure change of the pulse wave detection air bag, and a bypass channel branched from and connected between the first pipe and the second pipe, the apparatus comprising pulse wave detecting unit that obtains a pulse wave signal by detecting a pulse wave superposed on the cuff pressure signal, blood pressure detecting unit that determines a blood pressure value based on the cuff pressure signal and the pulse wave signal, and blood pressure display unit that displays the blood pressure value, wherein the first pipe is connected to the sub air bag, and a rod shape member which elastically deforms to be entirely foldable is inserted in a communicating portion between the sub air bag and the occluding air bag, thereby allowing the occluding air bag and the sub air bag to keep communicating with each other even when folded by the rod shape member.

There is also provided the blood pressure measuring apparatus, wherein the sub air bag and the occluding air bag are formed by using two soft sheet materials to be integrated, and integrally formed by welding entire peripheral edges with the rod shape member sandwiched therebetween.

There is also provided the blood pressure measuring apparatus, wherein the pulse wave detection air bag is integrally formed from a third closed bag formed into a flat rectangular shape by using a soft sheet material, and the second pipe having an open end communicating with the third closed bag.

There is also provided a cuff comprising a cuff member configured to be attached to and detached from a blood pressure measurement portion, an occluding air bag which is laid inside the cuff member and compresses the whole blood pressure measurement portion, a sub air bag which is laid on the occluding air bag and compresses a side of the blood pressure measurement portion which is close to a heart, and a pulse wave detection air bag which is laid on the occluding air bag, compresses a downstream side of a blood vessel in the blood pressure measurement portion, and detects a pulse wave generated by a heart beat generated downstream of the cuff, wherein between the sub air bag and the occluding air bag, a rod shape member which elastically deforms to be entirely foldable is inserted in a communicating portion between the sub air bag and the occluding air bag, thereby allowing the occluding air bag and the sub air bag to communicate with each other even when folded by the rod shape member.

There is also provided a method of manufacturing a cuff including a cuff member configured to be attached to and detached from a blood pressure measurement portion, an occluding air bag which is laid inside the cuff member and compresses the whole blood pressure measurement portion, a sub air bag which is laid on the occluding air bag and compresses a side of the blood pressure measurement portion which is close to a heart, and a pulse wave detection air bag which is laid on the occluding air bag, compresses a downstream side of a blood vessel in the blood pressure measurement portion, and detects a pulse wave generated by a heart beat generated downstream of the cuff, wherein between the sub air bag and the occluding air bag, a rod shape member which elastically deforms to be entirely foldable is inserted in a communicating portion between the sub air bag and the occluding air bag, thereby allowing the occluding air bag and the sub air bag to communicate with each other even when folded by the rod shape member.

Other features of the present invention will be apparent from the best mode for carrying out the invention and the accompanying drawings.

Effects of the Invention

In the present invention, because the air supply/exhaust pipe connected to the sub air bag positioned upstream of the occluding air bag which positioned between the occluding air bag and a measurement portion can be extracted outside the occluding air bag, it is possible to prevent the pipe from being positioned between the occluding air bag and measurement portion (skin). Therefore, this makes it possible to prevent the abnormality of air supply to or exhaust from the sub air bag caused by kink or folding of the pipe. In addition, variations in supply amount of air to the sub air bag caused by kink or folding of the pipe can be prevented. This makes it possible to prevent variations in correction of the difference between the compressing forces of a middle portion and upstream portion of the occluding air bag caused by the sub air bag.

Furthermore, because there is no necessity that a tube having high hardness is used to prevent kinking of the pipe, it is possible to avoid insufficient occlusion by the occluding air bag, or internal bleeding of the skin caused by a large wrinkle formed on the occluding air bag if a tube having high hardness is used. In addition, the number of members to be used in the piping decreases. In a step of welding by dielectric heating for the occluding air bag, therefore, it is possible to produce the sub air bag and connect the air supply/exhaust pipe to the sub air bag at once. This simplifies the cuff manufacturing process, improves the manufacturing quality, and reduces the manufacturing cost.

Other features and advantages of the present invention will be apparent from the following explanation taken in conjunction with the accompanying drawings. Note that the same reference numerals denote the same or similar parts in the accompanying drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 8 is a flowchart for explaining the operation of the blood pressure measuring apparatus.

EXPLANATION OF REFERENCE NUMERALS

Figure 1:
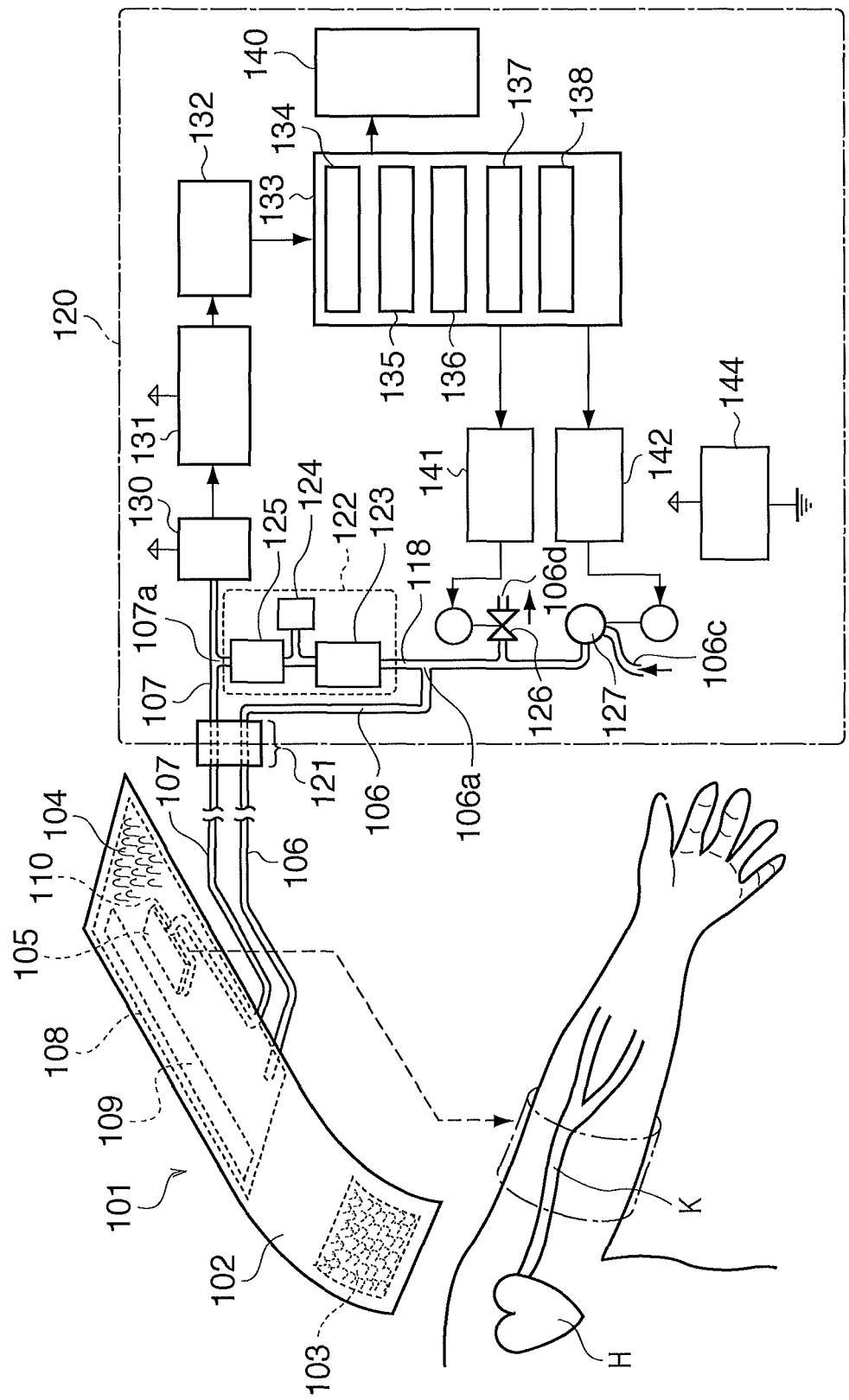
FIG. 1 is a block diagram showing a blood pressure measuring apparatus of an embodiment of the present invention.

101 . . . cuff (cuff main body)
102 . . . cuff member
103, 104 . . . hook-and-loop fastener
105 . . . interrupting device
106 . . . first pipe
107 . . . second pipe
108 . . . occluding air bag
109 . . . sub air bag
110 . . . pulse wave detection air bag
111 . . . rod shape member
118 . . . bypass channel
120 . . . main boy
122 . . . acoustic impedance device
123 . . . first coil
125 . . . second coil
124 . . . volume member
H . . . heart
K . . . artery
M . . . pulse wave

BEST MODE FOR CARRYING OUT THE INVENTION

An embodiment of the present invention will be explained below with reference to the accompanying drawings. FIG. 1 is a block diagram showing a blood pressure measuring apparatus of an embodiment of the present invention.

In the embodiment shown in FIG. 1, a cuff main body 101 includes a cloth cuff member 102 that can be attached to and detached from a blood pressure measurement portion including the upper arm. A male hook-and-loop fastener 103 indicated by the broken lines is formed at the end portion of the back surface of the cuff member 102, and a female hook-and-loop fastener 104 is formed at the end portion of the upper surface (of the cuff member 102). The cuff main body 101 can be attached by wrapping the cuff member 102 around the upper arm as shown in FIG. 1, and putting on the hook-and-loop fasteners. The hook-and-loop fasteners are merely examples, so another fastened member can also be used. It is also possible to use a cylindrical arm-in cuff member into which the upper arm is inserted.

On the blood pressure measurement portion side of the cuff member 102, an occluding air bag 108 indicated by the dotted lines is laid to compress the whole blood pressure measurement portion. Also, on that side of the occluding air bag 108 which is brought into contact with the blood pressure measurement portion, a sub air bag 109 indicated by the broken lines is laid to have a smaller width in order to compress that side of the blood pressure measurement portion which is close to a heart H. The occluding air bag 108 and sub air bag 109 are connected to a first pipe 106 made of a soft tube that forms one pipe connected to a pump 127 and valve 126 as a pressurizing/depressurizing unit and a solenoid on-off valve 126. Each air bag can be pressurized by supplying external air from an opening 106c by driving a motor M of the pump 127, and depressurized by exhausting air from an opening 106d by supplying an electric current to the solenoid on-off valve 126.

On that side of the occluding air bag 108 which is brought into contact with the blood pressure measurement portion, a pulse wave detection air bag 110 (pulse wave detection cuff) for detecting a pulse wave by compressing the downstream side of the blood vessel of the blood pressure measurement portion is laid on an interrupting device 105 (to be described later). The pulse wave detection air bag 110 is connected to a second pipe 107 made of a soft tube. The second pipe 107 can be detached together with the first pipe 106 described above from the main body 120 by a connector 121. Although the first pipe 106 and the second pipe 107 is detachably connected by the connector 121, these two pipes may also be connected directly.

Branched portions 106a and 107a of the first pipe 106 and second pipe 107 are connected to a bypass channel 118. The pulse wave detection air bag 110 is pressurized and depressurized via the bypass channel 118.

Also, a pressure sensor 130 is connected to the second pipe 107. The pressure sensor 130 is a cuff pressure detecting unit that obtains a cuff pressure signal from an occluding pressure in the occluding air bag 108 in which its superimposed pulse wave component is attenuated by an acoustic filter 122 of the first pipe 106, and a pressure change of the pulse wave detection air bag 110. A pressure measuring unit 131 for conversion into an analog electrical signal is connected to the pressure sensor 130, and an A/D converter 132 is connected to the pressure measuring unit 131. In this arrangement, a digital signal is output as the cuff pressure signal to a central control unit 133.

The central control unit 133 includes a ROM and RAM storing various computer-readable control programs, and incorporates, as the control programs, a pulse wave processing unit 134, cuff pressure processing unit 135, blood pressure measuring unit 137, and display control unit 138 serving as a pulse wave detecting unit that obtains a pulse wave signal by detecting a pulse wave to be superposed on the cuff pressure signal, and a blood pressure detecting unit that determines a blood pressure value based on the cuff pressure signal.

The central control unit 133 is connected to a liquid crystal display unit 140 as a blood pressure display unit that displays a blood pressure value, a pump driving unit 142 for controlling driving of the pump 127, and a valve driving control unit 141 for opening and closing the solenoid on-off valve 126. The central control unit 133 is designed to be able to perform operations necessary for blood pressure measurement when electric power is supplied from a power supply unit 144 including a dry battery.

On the other hand, the bypass channel 118 is connected to an acoustic impedance unit 122 indicated by the broken lines shown in FIG. 1. The acoustic impedance unit 122 includes first and second acoustic resistances made of capillaries, an acoustic inertance, and an acoustic compliance.

This connection to the bypass channel 118 as described above attenuates a pressure fluctuation generated by the volume change of the blood vessel on the upstream side of the cuff and the cuff pressure contained in the pressure signal of the sub air bag and occluding air bag when the cuff pressure is equal to or higher than the systolic blood pressure during depressurization.

Figure 2:
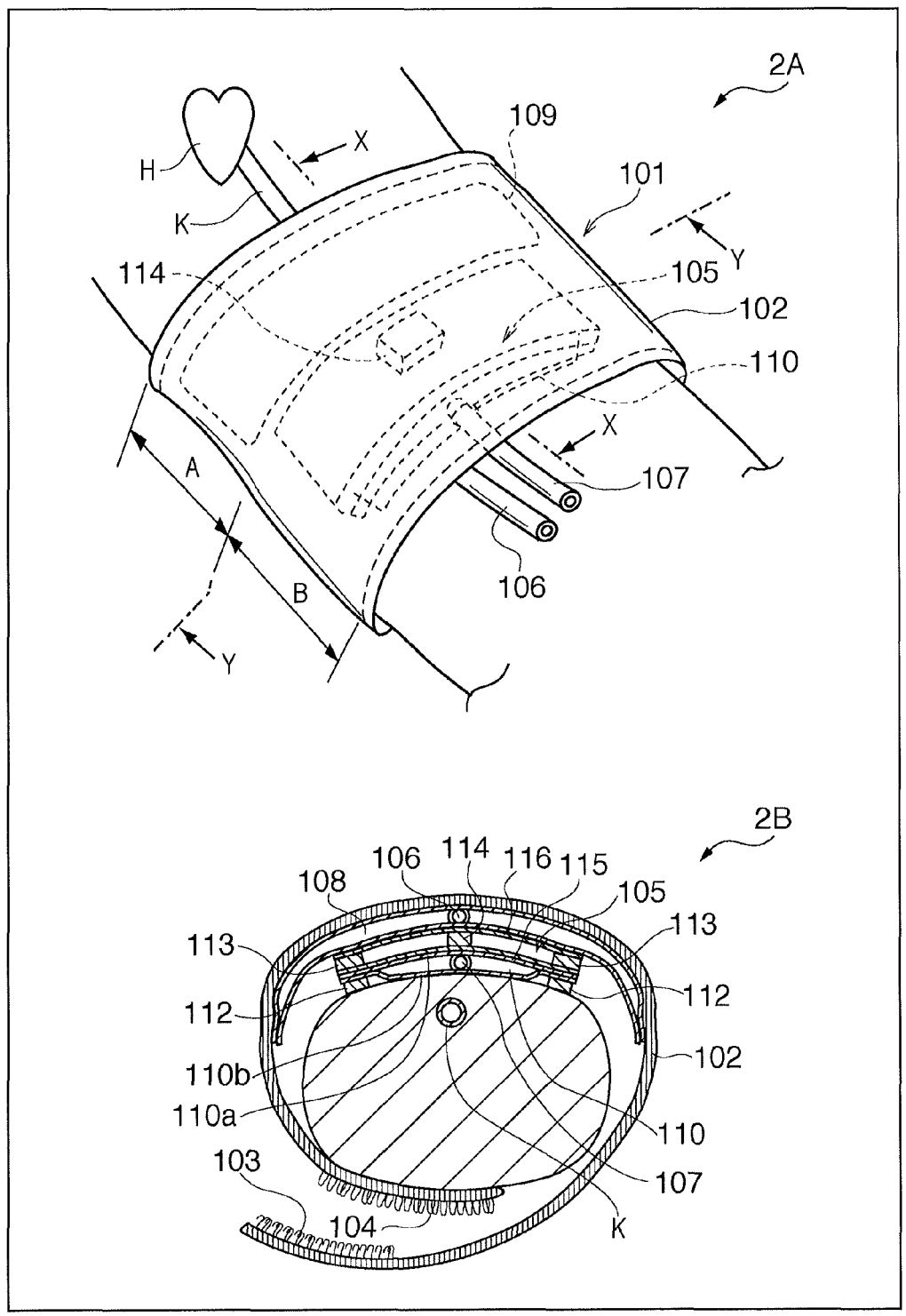
FIG. 2A is a perspective view showing an outer appearance after a cuff main body 101 is attached to the upper arm.
FIG. 2B is a sectional view taken along a line Y-Y in FIG. 2A.
Figure 3:
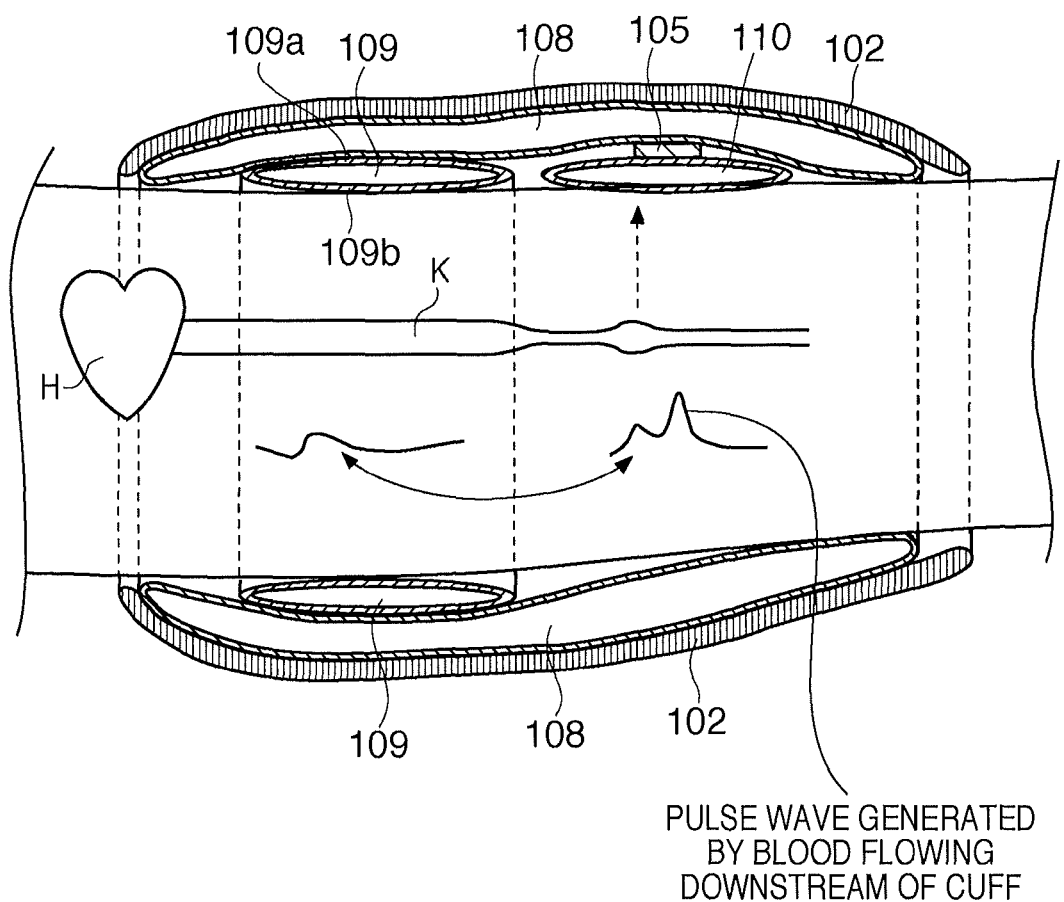
FIG. 3 is a sectional view taken along a line X-X in FIG. 2A.

2A of FIG. 2 is a perspective view showing an outer appearance when the cuff main body 1 is attached to the upper arm, and 2B of FIG. 2 is a sectional view taken along a line Y-Y in 2A. FIG. 3 is a sectional view taken along a line X-X in 2A of FIG. 2.

Referring to FIGS. 2 and 3, the same reference numerals as in FIG. 1 denote the arrangements and parts already explained above, and a repetitive explanation will be omitted. First, in 2A of FIG. 2, when the cuff main body 101 is attached to the upper arm, the sub air bag 109 is positioned on the heart side, and the pulse wave detection air bag 110 is positioned on the artery in a measurement portion with the interrupting device 105 interposed between them. Also, the first pipe 106 and second pipe 107 are extracted parallel outside as shown in FIG. 2.

In 2B of FIG. 2, the interrupting device 105 is installed to form an air layer between the occluding air bag 108 and pulse wave detection air bag 110. The interrupting device 105 prevents the oscillation, caused in the occluding air bag by the heart beat, transmitted to the pulse wave detection air bag 110.

Figure 4:
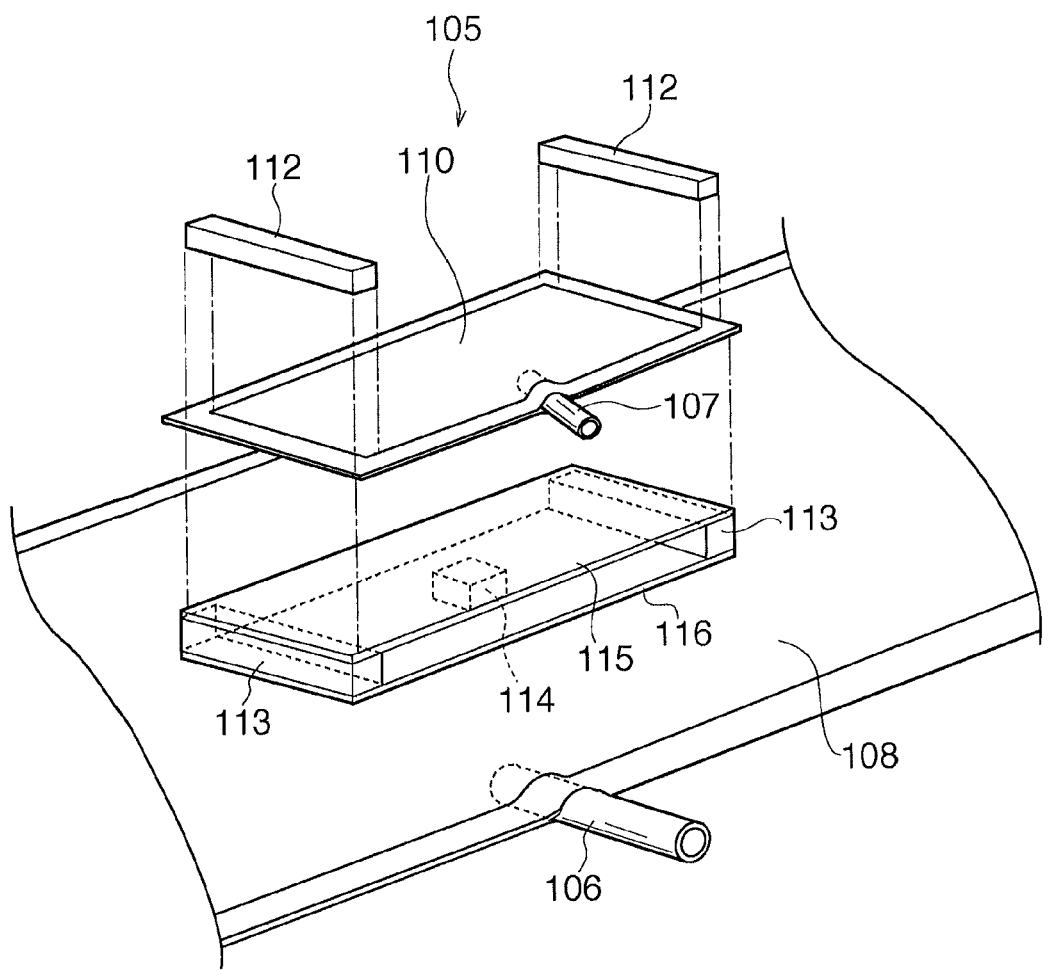
FIG. 4 is an elevational exploded view of an interrupting device 105.

In addition, it explains referring to an elevational exploded view of FIG. 4, therefore, the interrupting device 105 includes a first sheet member 115 made of a soft sheet material and having the surface shape of a closed bag of the pulse wave detection air bag 110, and a second sheet member 116 having the surface shape of the closed bag of the pulse wave detection air bag 110 and positioned on a closed bag of the occluding air bag 108, and first spacer members 113 formed between short sides at the end portions of the first sheet member 115 and second sheet member 116 and having the length of the short sides. Also, a square second spacer member 114 is formed in the middle of the first sheet member 115 and second sheet member 116. The second spacer member 114 prevents adhesion of the first and second sheet members after attachment, thereby maintaining the air layer having the same thickness as shown in 2B of FIG. 2.

In FIG. 4, third spacer members 112 having the length of the short sides of the closed bag are further formed on the short sides at the ends of the closed bag, so that a predetermined amount or more of air enters the pulse wave detection air bag 110.

Figure 5:
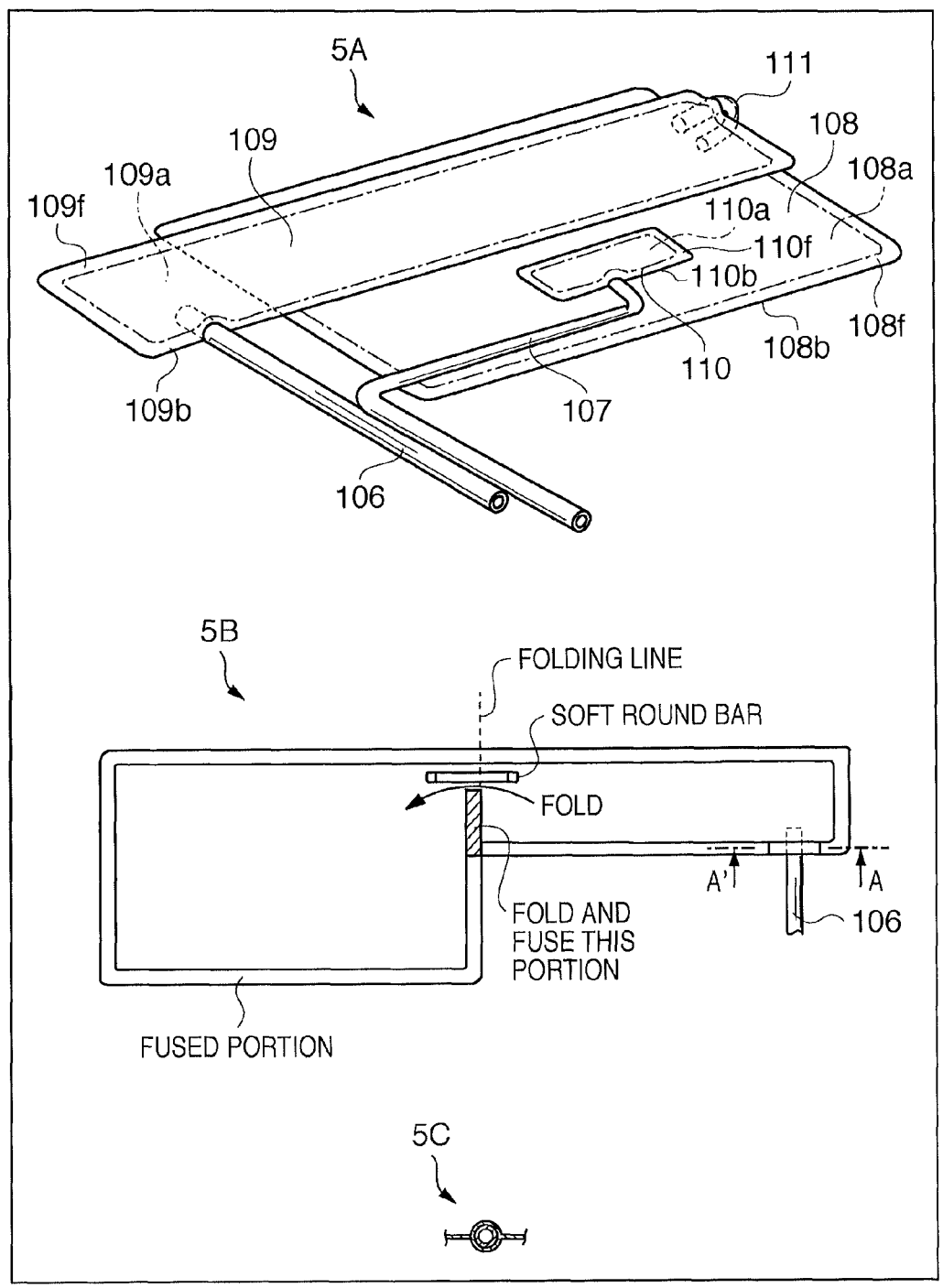
FIG. 5A is a perspective view showing the outer appearances of an occluding air bag 108 and sub air bag 109.
FIG. 5B is a developed view of the occluding air bag 108 and sub air bag 109.
FIG. 5C is a sectional view taken along a line A-A in FIG. 5B.

Referring to a perspective view showing the outer appearances of the occluding air bag 108 and sub air bag 109 in 5B of FIG. 5, the sub air bag 109 is not limited to the size shown in FIG. 5, and may also partially extend from the occluding air bag 108. The sub air bag 109 may also have the same length as that of the occluding air bag 108, provided that the sub air bag 108 is correctly positioned on the heart side.

The sub air bag 109 is prepared as an integrally molded closed bag obtained by (vertically) sandwiching the first pipe 106 and an entirely foldable rod shape member 111 by upper and lower sheet members 109a and 109b made of a soft resin, and continuously welding a flange 109f and the first pipe 106 (see 5C of FIG. 5) with heating or dielectric heating, thereby closing the interior and forming a communicating portion along the longitudinal direction of the rod shape member 111. At the same time, the occluding air bag 108 is also prepared as an integrally molded closed bag obtained by (vertically) sandwiching the rod shape member 111 by upper and lower sheet members 108a and 108b made of a soft resin, and continuously welding a flange 108f with heating or dielectric heating as shown in FIG. 5, thereby closing the interior. After that, when one closed bag is folded in the direction of the arrow, the rod shape member 111 is also folded at about 180° at the same time, thereby obtaining a state as shown in 5A of FIG. 5.

This arrangement obviates the need for a pipe separately connected to the occluding air bag 108 in the conventional cuff, thereby cutting the cost accordingly. In addition, at the time of pressurization, the sub air bag 109 is first expanded, and the occluding air bag 108 is expanded by pressurization after that.

Consequently, it is possible to effectively prevent the tendency to decrease the amount of air supplied to the sub air bag 109, and prevent the deterioration of the pulse wave attenuating effect obtained by the sub air bag 109. Also, since the air amount in the sub air bag 109 can be held constant, variations of the pulse wave attenuating effect can be prevented. Furthermore, in the conventional arrangement, the residual air amount in the sub air bag 109 sometimes varies in accordance with the residual air amount in each air bag at the time of pressurization. However, the above-mentioned arrangement can completely eliminate this tendency.

After the state shown in 5A of FIG. 5 is obtained by folding the rod shape member 111 and laying the air bags so that they overlap each other as described above, the pulse wave detection air bag 110 connected to the second pipe 107 is placed. The sub air bag 109 is formed by integrating a first closed bag formed into a flat rectangular shape shown in FIG. 5 by using a soft material, and the first pipe 106 having an open end communicating with the first closed bag. The occluding air bag 108 is formed by a second closed bag formed into a flat rectangular shape larger than the first closed bag by using a soft material. The occluding air bag 108 is integrally welded by positioning one end of the rod shape member 111 in the first closed bag, and the other end of a middle pipe in the second closed bag.

It is of course also possible to integrally form the pulse wave detection air bag 110 by (vertically) sandwiching the second pipe 107 by upper and lower sheet members 110a and 110b made of a soft material, and continuously adhering a flange 110f.

Referring to FIG. 3 again, the sub air bag 109 (upstream side of the cuff) cuff is attached on the side of the left ventricle. Also, since the interrupting device 105 is installed to form an air layer between the occluding air bag 108 and pulse wave detection air bag 110, it is possible to effectively prevent the oscillation of the occluding air bag 108, which is generated by the volume change of the blood vessel on the upstream side of the cuff, from being transmitted to the pulse wave detection air bag 110.

Conventionally, a damper formed by a stacked rigid plate member with large rigidity and foamed urethane is installed instead of the interrupting device 105. However, the damping characteristic of this damper is sometimes deterioration when compressed by the cuff pressure. This makes it impossible to obtain a damping characteristic that particularly absorbs oscillations close to the heart beat frequency.

By contrast, since the air layer as described above is formed and can be kept uncollapsed, it is possible to obstruct the spread of oscillation from the occluding air bag 108.

Consequently, a pulse wave M generated downstream of the blood vessel below the cuff when the internal pressure of the occluding air bag 108 becomes slightly lower than the systolic blood pressure can be detected at a high S/N ratio. In addition, cooperation with the acoustic impedance unit 122 (to be described later) prevents a pulse wave generated upstream of the cuff when the cuff pressure is higher than the blood pressure from being transmitted between the parts of the cuff. Since this attenuates a pulse component as noise, it is possible to increase the S/N ratio and accurately detect only a pulse wave change caused by the volume change of the artery resulting from the blood flow that is output downstream of the cuff at the measurement timing.

Figure 6:
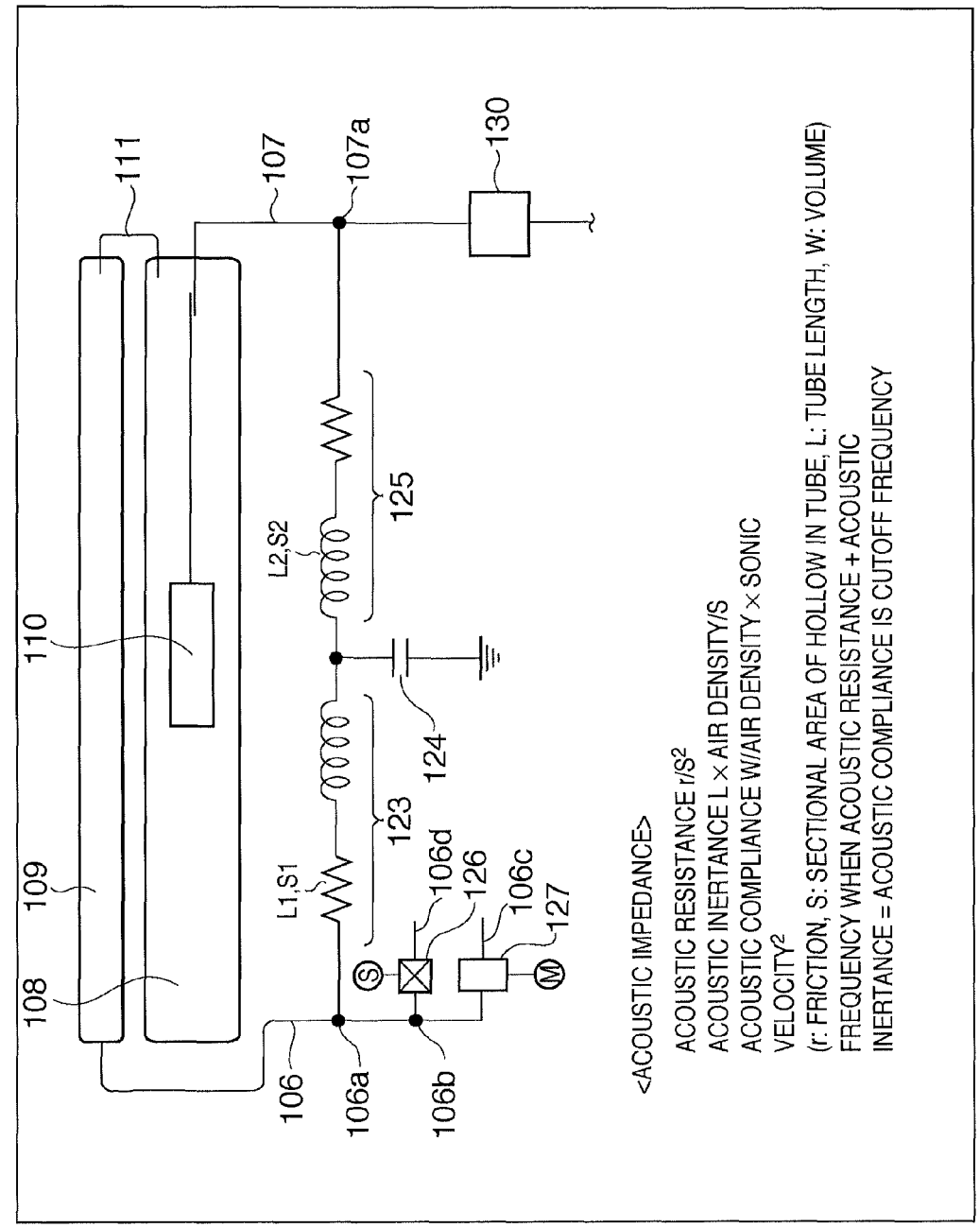
FIG. 6 is an exemplary view of an acoustic impedance unit 122 connected to a bypass channel 118.

FIG. 6 is an exemplary view of the acoustic impedance unit 122 connected to the bypass channel 118 described above. In FIG. 6, the same reference numerals as above denote the arrangements or parts already explained, and a repetitive explanation will be omitted. A first coil member 123 formed by winding a tube having a first channel length L1 and first inner diameter hole sectional area S1 into the form of a coil is connected to the branched portion 106a of the first pipe 106. The first acoustic resistance is obtained from a relation of friction r/S2, and the first acoustic inertance is obtained from a relation of L1*air density/S.

On the other hand, a second coil member 125 formed by winding a tube having a second channel length L2 and second inner diameter hole sectional area S2 into the form of a coil is connected to the branched portion 107a of the second pipe 107. The second acoustic resistance is obtained from a relationship of friction $r/S2^2$, and the second acoustic inertance is obtained from a relation of L2*air density/S2.

The whole acoustic impedance unit 122 is formed such that the acoustic compliance is obtained from a relation of volume W/air density*sonic velocity$^2$ by a volume member having a volume portion connected between the first coil member 123 and second coil member 125. Noise is attenuated as air oscillation by making the cutoff frequency equal to or close to the heart beat oscillation. By thus winding the coils, it is possible to achieve a volume about 1/10 the conventional buffer tank volume, and downsize the entire apparatus.

Figure 7:
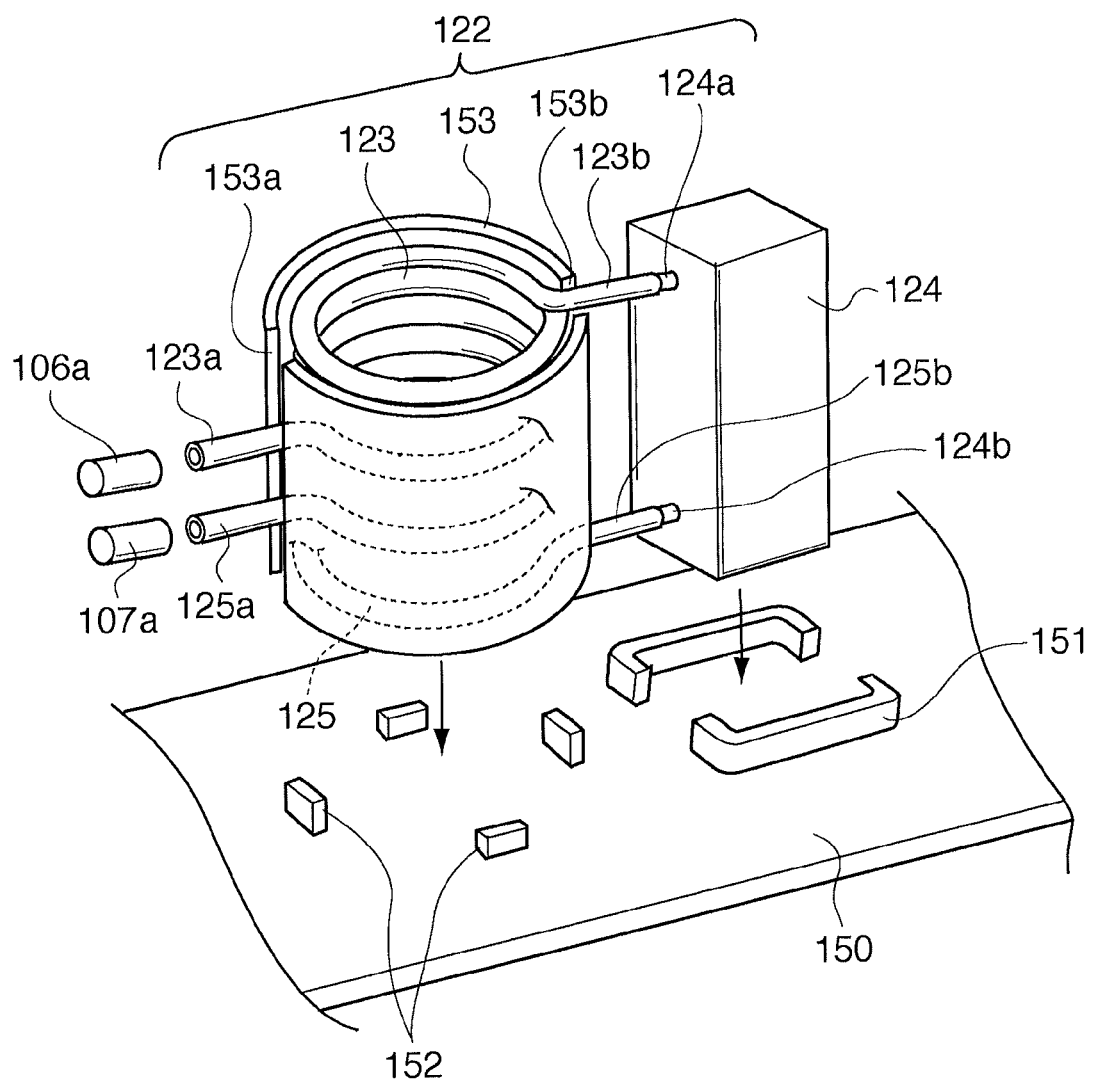
FIG. 7 is a perspective view showing the outer appearance of the acoustic impedance unit 122.

FIG. 7 is a perspective view showing an arrangement for downsizing. A first entrance end portion 123a and first exit end portion 123b of the first coil member 123 and a second entrance end portion 125a and second exit end portion 125b of the second coil member 125 indicated by the broken lines are vertically aligned. A cylindrical member 153 having a pair of vertical slits 153a and 153b for accommodating the coil members from this state is installed, and the first coil member 123 and second coil member 125 are accommodated as they are stacked inside the cylindrical member 153, as shown in FIG. 7.

On the other hand, fixing portions 152 are formed on a mounting base 150 of the main body, so the cylindrical member 153 can be fixed as it is moved downward. In addition, a volume member 124 having connecting openings 124a and 124b in positions connected to the first exit end portion 123b and second exit end portion 125b is installed adjacent to the cylindrical member 153. The volume member 124 can directly be connected to the cylindrical member 153, as shown in FIG. 7. The volume member 124 is also fixed as it is fitted in fixing portions 151 on the mounting base 150.

In the above arrangement, the acoustic impedance unit 122 can attenuate a pulse wave component of normally 1 to 1.5 Hz, that is, 60 to 70 beats/min detected by the sub air bag and occluding air bag, by adjusting the inner diameters of the coil members 123 and 125 and the volume of the volume member 124. Consequently, in the pulse wave detection air bag 110, it is possible to increase the S/N ratio and accurately detect only a pulse wave change caused by the volume change of the artery on the downstream side of the cuff at the systolic blood pressure measurement timing.

The cuff main body 101 having the above arrangement can be used in various type of blood pressure measuring apparatuses. For example, the blood pressure measuring apparatus shown in FIG. 1 can be operated as shown in a blood pressure measuring routine flowchart of FIG. 8 by reading out the stored control programs by a computer.

First, the blood pressure measuring apparatus is activated, the cuff main body 101 is attached as shown in FIG. 2, and a start switch (not shown) is pressed. Consequently, in step S101, the valve driving unit 141 supplies an electric current to the on-off valve 126 to open it, thereby exhausting residual air from each air bag. When this residual air exhaustion is complete, zero setting (initialization) of the pressure sensor is performed, and the on-off valve 126 is closed in step S102, thereby making preparations for measurement.

After that, in step S103, the pump 127 is continuously driven by setting a set pressure P at 20~30 mmHg higher than 180 mmHg as an expected systolic blood pressure. In step S104, whether the pressure of the occluding air bag 108 and sub air bag 109 has reached the set pressure P is checked by a signal from a cuff pressure detector, and pump driving is continued until the set pressure is reached. When the set pressure P is reached, pump driving is stopped in step S105. When the pressure of the cuff main body 101 has reached the set pressure P, the process advances to step S106 to cause a depressurization controller to start depressurization by using the signal from the cuff pressure detector, such that the depressurization rate is 2 to 3 mmHg/sec.

Subsequently, the detection of the cuff pressure is stored in step S107, and the detection of a pulse wave and a cuff pressure signal are started in step S108. Then, the process advances to step S109, and a pulse wave signal detected by a pulse wave detector is supplied to an internal storage unit of a blood pressure detector, and the cuff pressure and pulse wave amplitude are paired and stored. In step S110, an abrupt increase in pulse wave amplitude is detected by, for example, comparing the pulse wave amplitude with the average value of the past amplitude values, and detecting at a point at which the pulse wave amplitude becomes twice the average value as a systolic blood pressure point. Steps S106 to S110 are repetitively performed until the systolic blood pressure is detected.

Then, the process advances to step S111, and the cuff pressure is depressed sequentially. In step S112, if the blood pressure detector detects a phenomenon in which the pulse wave amplitude decreases for every heart beat, a pulse wave equal to or lower than a predetermined ratio of a maximal pulse wave value, for example, 60% is detected, and the corresponding cuff pressure is determined as the diastolic pressure. When this diastolic pressure is determined, the depressurization controller performs rapid exhaust. In step S113, the systolic blood pressure value and diastolic pressure value thus determined are displayed on the blood pressure display unit 140, and the series of blood pressure measurement operations are completed.

As described above, a pulse wave generated on the peripheral side when the internal pressure of the occluding air bag becomes lower than the blood pressure can be detected without using any fluid resistance as a stop having a large pressure loss. Therefore, the measurement time can also be shortened because can be depressed high depression rate (2~3 mmHg/sec).

The present invention is not limited to the above embodiment and various changes and modifications can be made without departing from the spirit and scope of the invention. Therefore, to apprise the public of the scope of the present invention, the following claims are appended.

The invention claimed is:

1. A method of manufacturing a cuff including:
   providing a cuff member configured to be attached to and detached from a blood pressure measurement portion,
   laying an occluding air bag inside the cuff member such that the occluding air bag compresses the whole blood pressure measurement portion,
   laying a sub air bag on the occluding air bag and forming the sub air bag with a width which is shorter than a width of the occluding air bag in order to compress a side of the blood pressure measurement portion which is close to a heart, and
   laying a pulse wave detection air bag on the occluding air bag, such that the pulse wave detection air bag compresses a downstream side of a blood vessel in the blood pressure measurement portion, and detects a pulse wave generated by a heart beat generated downstream of the cuff,
   inserting a rod shape member which elastically deforms to be entirely foldable in a communicating portion between the sub air bag and the occluding air bag, thereby allowing the occluding air bag and the sub air bag to communicate with each other even when the sub air bag is folded into the occluding air bag at 180 degrees while folding the rod shape member at the same time,
   providing the occluding air bag and the sub air bag such that, when the occluding air bag and the sub air bag are pressurized after being attached to an upper arm, the occluding air bag laid inside the cuff member is expanded after the sub air bag is expanded,
   preparing the sub air bag and the occluding air bag as an integrally molded closed bag such that, when one of the sub air bag or the occluding air bag is folded into the other air bag, the rod shape member is also folded at the same time, and
   providing an interrupting device between the sub air bag and the occluding air bag.

2. A method of manufacturing a cuff including a cuff member configured to be attached to and detached from a blood pressure measurement portion, said method comprising:
   forming a connecting sub air bag and an occluding air bag by using two soft sheet materials to be integrated and integrally forming by welding the entire peripheral edges such that the connection is a communicating channel between the sub air bag and occluding bags,
   inserting a rod shape member which elastically deforms to be entirely foldable in the communicating channel between the sub air bag and the occluding air bag, thereby allowing the occluding air bag and the sub air bag to communicate with each other even when folded by the rod shape member,
   laying the occluding air bag inside the cuff member such that the occluding air bag compresses the whole blood pressure measurement portion,
   laying the sub air bag on the occluding air bag by folding the sub air bag onto the occluding air bag such that when the sub air bag is folded onto the occluding air bag, the rod shape member is also folded at the same time,
   laying a pulse wave detection air bag on the occluding air bag, such that the pulse wave detection air bag compresses a downstream side of a blood vessel in the blood pressure measurement portion, and detects a pulse wave generated by a heart beat generated downstream of the cuff, and
   wherein the sub air bag has a width which is shorter than a width of the occluding air bag in order to compress a side of the blood pressure measurement portion which is close to a heart, and
   providing an interrupting device between the sub air bag and the occluding air bag.

\* \* \* \* \*